US008524781B2

(12) United States Patent
Kaschula et al.

(10) Patent No.: US 8,524,781 B2
(45) Date of Patent: Sep. 3, 2013

(54) ORGANOSULFUR COMPOUNDS, A METHOD OF MAKING ORGANOSULFUR COMPOUNDS AND THEIR USE FOR INHIBITING THE GROWTH OF TUMOUR CELLS

(75) Inventors: Catherine Hart Kaschula, Cape Town (ZA); Roger Hunter, Cape Town (ZA); Mohamed Iqbal Parker, Cape Town (ZA)

(73) Assignee: University of Cape Town, Cape Town (ZA)

( * ) Notice: Subject to any disclaimer, the term of this patent is extended or adjusted under 35 U.S.C. 154(b) by 91 days.

(21) Appl. No.: 13/057,960

(22) PCT Filed: Aug. 5, 2009

(86) PCT No.: PCT/IB2009/053399
§ 371 (c)(1),
(2), (4) Date: Apr. 23, 2011

(87) PCT Pub. No.: WO2010/016011
PCT Pub. Date: Feb. 11, 2010

(65) Prior Publication Data
US 2011/0190368 A1 Aug. 4, 2011

(30) Foreign Application Priority Data
Aug. 5, 2008 (ZA) .................. 2008/06780

(51) Int. Cl.
*A61K 31/105* (2006.01)
*C07C 325/02* (2006.01)

(52) U.S. Cl.
USPC ........................................... 514/707; 568/20

(58) Field of Classification Search
USPC .......................................................... 568/20
See application file for complete search history.

(56) References Cited

U.S. PATENT DOCUMENTS

| 4,643,994 A | 2/1987 | Block et al. |
| 2003/0077264 A1 | 4/2003 | Goodrich |

FOREIGN PATENT DOCUMENTS

| EP | 0 185 324 A | 6/1986 |
| EP | 0 353 416 A2 | 2/1990 |
| JP | 1 224314 A | 9/1989 |
| WO | WO 02/04413 A1 | 1/2002 |
| WO | WO 2008/027912 A | 3/2008 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Theodorescu, et al. Document No. 148:347284 (2008) retrieved from CAPLUS.*
Goodrich. Document No. 138:326511 (2003), retrieved from CAPLUS.*
Yoshida, et al. Document No. 129:133631 (1998), retrieved from CAPLUS.*
Block, et al. Document No. 106:32678 (1986), retrieved from CAPLUS.*
Gallwitz, Helge et al.: "Ajoene Is an Inhibitor and Subversive Substrate of Human Glutathione Reductase and *Trypanosorna cruzi* Trypanothione Reductase: Crystallographic, Kinetic, and Spectroscopic Studies", *J.Med.Chem.*, 1999, 42, pp. 364-372.
Taylor, Peter et al.: "Ajoene inhibits both primary tumor growth and metastasis of B16/BL6 melanoma cells in C57BL/6 mice", *Cancer Letters*, 239, 2006, pp. 298-304.
Sendl, A. et al.: "Inhibition of cholesterol synthesis in vitro by extracts and isolated compounds prepared from garlic and wild garlic", *Atherosclerosis*, 94, 1992, pp. 79-95.
Block E., et al; Antithrombotic Organosulfur Compounds from Garlic; 1986; pp. 7045-7055; vol. 108, No. 22; Journal of the American Chemical Society, Japan.
Yoshida H., et al.; Antimicrobial activity of a compound isolated from an oil-macerated garlic extract; Journal; 1998; pp. 1014-1017; vol. 62, No. 5; Bioscience Biotechnology Biochemistry, Japan Society for Bioscience, Biotechnology, and agrochemistry, Tokyo, Japan.
Hunter R., et al.; Substituted ajoenes as novel anti-cancer agents; Journal; 2008; pp. 5277-5279; vol. 18, No. 19; Bioorganic & Medicinal Chemistry, Pergamon, Elsevier Science, GB; Department of Chemistry, University of Cape Town, South Africa.
Peter Taylor, et al.; Ajoene inhibits both primary tumor growth and metastasis of B16/BL6 melanoma cells in C57BL/6; Article; 2006; pp. 298-304; cancer letters, vol. 239, issue 2; cancer letters.
Scharfenberg K., et al.; The cytotoxic effect of ajoene, a natural product from garlic, investigated with different cell lines; Article; 1990; pp. 103-108; vol. 53, issues 2-3; Cancer Letters.

(Continued)

*Primary Examiner* — Shawquia Young
(74) *Attorney, Agent, or Firm* — Frommer Lawrence & Haug LLP; Ronald R. Santucci

(57) ABSTRACT

Organosulfur compounds of the general formula (2) are described, wherein $R_1$ and $R_2$ are linear or branched C1-C5 alkyl; linear or branched C1-C5 alkenyl with the proviso that $R_1$ is not prop-1-enyl (allyl); substituted linear or branched C1-C5 alkenyl or substituted linear or branched C1-C5 alkyl, in which the substituents are selected from $OR_3$, $NR_4R_5$, $COOR_6$, $CON-R_7R_8$, in which $R_3$ is selected from H, $COR_9$, para-methoxybenzyl and trialkylsilyl, in which $R_9$ is alkyl or substituted alkyl; $R_4$ N and $R_5$ are alkyl or $R_4$ and $R_5$ together form a phthalimido group; $R_6$ is alkyl or substituted alkyl; and $R_7$ and $R_8$ are alkyl or substituted alkyl; substituted or unsubstituted aromatic specifically where $R_1$ and $R_2$ are benzyl, para-methoxybenzyl and/or ortho,para-methoxybenzyl and substituted or unsubstituted heteroaromatic. The compounds can be used for inhibiting the growth of tumor cells and for treating cancer. A pharmaceutical composition and a method of preparing the compounds are also described.

(2)

$$R_1-\underset{\underset{O}{\|}}{S}-\diagup\diagdown-S-S-R_2$$

24 Claims, No Drawings

(56) References Cited

OTHER PUBLICATIONS

Li M., et al.; Antitumor activity of Z-ajoene, a natural compound purified from garlic; antimitotic and microtubule-interaction properties; Carcinogenesis; 2002; pp. 573-579; vol. 23 No. 4 National Research Laboratories of Natural and Biomimetic Drugs, Peking University, Beijing ROC.

Kaschula K., et al.; Anti-Proliferative Activity of Synthetic Ajoene Analogues on Cancer Cell-Lines; Anti-Cancer Agents in Medicinal Chemistry-Anti-Caner Agents; 2011; pp. 260-266; vol. 11; Bentham Science Publishers.

Tilli C.M., et al.; The garlic-derived organosulfur component ajoene decreases basal cell carcinoma tumor size by inducing apoptosis; Arch Dermatol Res; 2003; 295(3): pp. 117-123; Research Institute Growth and Development.

Nishikawa T., et al.; Inhibition by Ajoene of Skin-tumor Promotion in Mice; Bioscience, Biotechnology and Biochemistry; 2002; pp. 2221-2223; vol. 66 No. 10; Biodevelopment Division, Central Institute, Nagoya Seiraku Co., Ltd.

Kaschula C., et al.; Structure-activity studies on the anti-proliferation activity of a analogues in WHCO1 oesophageal cancer cells; Elsevier; 2012; pp. 236-254; vol. 50; European Journal of Medicinal Chemistry.

\* cited by examiner

ORGANOSULFUR COMPOUNDS, A METHOD OF MAKING ORGANOSULFUR COMPOUNDS AND THEIR USE FOR INHIBITING THE GROWTH OF TUMOUR CELLS

This application is a 371 of PCT/IB2009/053399 filed on Aug. 5, 2009, published on Feb. 11, 2010 under publication number WO 2010/016011 A and claims priority benefits of South African Patent Application No. 2008/06780 filed Aug. 5, 2008, the disclosure of which is incorporated herein by reference.

BACKGROUND OF THE INVENTION

This invention relates to new compounds, to compounds useful for the inhibition of the growth of tumour cells, to a new process for the synthesis of said compounds, to the use of the compounds in the preparation of medicaments for the inhibition of the growth of tumour cells, and to methods for the inhibition of the growth of tumour cells.

Garlic (*allium sativum*) dietary supplements have a demonstrated ability to reduce the risk of cancer in human beings. The potential chemo-preventative effect of garlic has in the past been the subject of various clinical trials. The outcomes of these trials were contradictory depending on the type of tumour examined and the garlic preparation used. This is due to the fact that crude extracts of garlic contain numerous organosulfur compounds with varying stability and biological activity.

Many of the organosulfur compounds present in garlic have been well characterized. These compounds include allyl disulfides, allyl thiosulfinates and cysteine sulfoxides. Upon maceration of the garlic bulb one of these organosulfides, S-allylcysteine-S-oxide (Olin), is converted to 2-propenethiosulfinate (allicin) by the enzyme allinase. Two molecules of allicin can then combine and rearrange by a thio-Claisen rearrangement to yield an E/Z mixture of 4,5,9-trithiadodeca-1,6,11-triene-9-oxide (E-ajoene and Z-ajoene), the structures of which are represented in Formulae 1.1 and 1.2 respectively. Structurally, ajoene contains interesting sulfoxide (S=O) and unusual vinyl disulfide (=S—S) motifs. Synthesis of ajoene can be conducted in vitro in low yield by thermal decomposition of allicin in an acetone-water mixture.

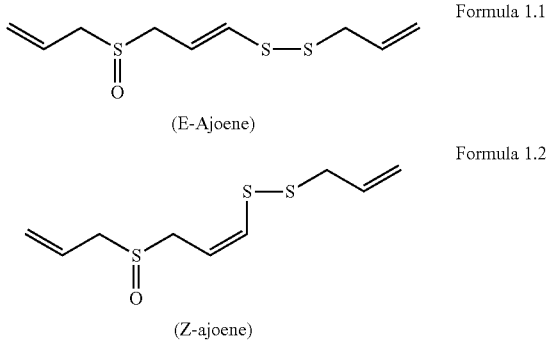

Ajoene has been shown to offer strong protection against TPA-promoted carcinogenesis on mouse skin, and to strongly inhibit metastasis to the lungs in the B16/BL6 melanoma tumour model in C57BL/6 mice. In one clinical trial topical application of ajoene to the tumours of a group of human patients with either nodular or superficial basal cell carcinoma caused a reduction in tumour size in a large percentage of subjects.

It has also been shown that ajoene is able to induce apoptosis in a number of tumour cell lines including human breast, bladder, colorectal, hepatic, prostate, lymphoma, leukemia and skin. Apoptosis is a form of physiological cell death characterized by chromatin condensation, cytoplasmic blebbing, and DNA fragmentation. Two major pathways mediating drug-induced apoptosis have been characterized. One involves the triggering of cell surface death receptors and the other the targeting of mitochondria without the involvement of a receptor/ligand system. It is hypothesized that ajoene induces apoptosis via the latter pathway. Ajoene has been shown to induce apoptosis and arrest HL60 leukemic cells in the $G_2/M$ phase of the cell cycle in a dose-dependent manner. Ajoene-treated leukemia cells undergo a time-dependent reduction in the anti-apoptotic Bcl-2 protein, resulting in the release of cytochrome C and activation of caspase 3. These results support the hypothesis that ajoene-induced apoptosis in leukemia cells proceeds via a mitochondria-dependent caspase cascade.

Ajoene has also been shown to decrease the expression of $\alpha 4\beta 1$ integrin in murine melanoma cells, and to induce complete disassembly of the microtubule network in HL60 cells.

SUMMARY OF THE INVENTION

According to a first embodiment of the invention, there is provided a compound of formula (2)

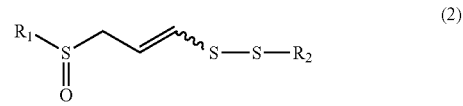

wherein:
$R_1$ and $R_2$ are
linear or branched C1-C5 alkyl;
linear or branched C1-C5 alkenyl, with the proviso that $R_1$ is not prop-1-enyl (allyl);
substituted linear or branched C1-C5 alkenyl; or
substituted linear or branched C1-C5 alkyl;
in which the substituents are selected from
$OR_3$;
$NR_4R_5$;
$COOR_6$;
$CONR_7R_8$;
substituted or unsubstituted aromatic;
substituted or unsubstituted heteroaromatic,
in which
$R_3$ is selected from H, $COR_9$, para-methoxybenzyl, and trialkylsilyl, in which $R_9$ is alkyl or substituted alkyl;
$R_4$ and $R_5$ are independently alkyl or $R_4$ and $R_5$ together form a phthalimido group;
$R_6$ is alkyl or substituted alkyl; and
$R_7$ and $R_6$ are independently alkyl or substituted alkyl.

The alkyl groups may be independently selected from methyl, ethyl, propyl, butyl, isopropyl and isobutyl.

The alkenyl groups may be independently selected from prop-1-enyl (allyl), 1-propenyl, 1-butenyl, 2-butenyl, 3-butenyl and 1-methyl-2-butenyl.

In particular, $R_1$ may be propyl, 3-hydroxypropyl, 3-phthalimidopropyl, tert-butyl, benzyl, para-methoxybenzyl, ortho,para-methoxybenzyl, 3-(para-methoxybenzyloxy)propyl, dansyl or 3-(tert-dimethylsilyloxy)propyl.

In particular, $R_2$ may be propyl, prop-1-enyl, para-methoxybenzyl, ortho,para-methoxybenzyl, benzyl or para-fluorobenzyl.

More particularly, $R_1$ may be propyl, 3-hydroxypropyl, 3-phthalimidopropyl, tert-butyl, benzyl, para-methoxybenzyl, ortho,para-methoxybenzyl, 3-(para-methoxybenzyloxy) propyl or 3-(tert-dimethylsilyloxy)propyl and $R_2$ may be prop-1-enyl.

More particularly, $R_1$ may be para-methoxybenzyl or ortho,para-methoxybenzyl and $R_2$ may be para-methoxybenzyl, ortho,para-methoxybenzyl, benzyl or para-fluorobenzyl.

Even more particularly, $R_1$ may be dansyl and $R_2$ may be propyl.

For example, particular compounds of formula (2) may be:
(E/Z)-4,5,9-trithiadodeca-1,6-diene-9-oxide (3),
(E/Z)-4,8,9-trithiadodeca-6,11-diene-1-ol-4-oxide (4),
(E/Z)-12-phthalimido-4,5,9-trithiadodeca-1,6-diene-9-oxide (5),
(E/Z)-10,10-dimethyl-4,5,9-trithiaundeca-1,6-diene-9-oxide (6),
(E/Z)-10-phenyl-4,5,9-trithiadeca-1,6-diene-9-oxide (7),
(E/Z)-10-(p-methoxyphenyl)-4,5,9-trithiadeca-1,6-diene-9-oxide (8),
(E/Z)-12-(p-methoxybenzyloxy)-4,5,9-trithiadodeca-1,6-diene-9-oxide (9),
(E/Z)-1-(p-fluorophenyl)-8-(p-methoxyphenyl)-2,3,7-trithiaocta-4-ene-7-oxide (10),
(E/Z)-1-(p-methoxyphenyl)-8-(p-methoxyphenyl)-2,3,7-trithiaocta-4-ene-7-oxide (11),
(E/Z)-1-phenyl-8-(p-methoxyphenyl)-2,3,7-trithiaocta-4-ene-7-oxide (12),
(E/Z)-1-(dansylamino)-4,5,9-trithiadodeca-6-ene-9-oxide (13),
(E/Z)-4,5,9-trithiadodeca-6-ene-9-oxide (14), or
(E/Z)-2,3,7-trithiadeca-4-ene-7-oxide (15).

The compound may be for use in a method of killing or inhibiting the growth of tumour cells and/or treating cancer, such as lung cancer, oesophageal cancer, cervical cancer or breast cancer.

According to a further embodiment of the invention, there is provided a pharmaceutical composition comprising a compound described above and a pharmaceutically acceptable carrier. The composition may be for use in killing or inhibiting the growth of tumour cells and/or for treating cancer.

According to a further embodiment of the invention, there is provided a method of making a compound of formula (2), the method including the steps of:
(i) acylating a compound of formula (16), wherein $R_1$ is as described in claim 1, with thiolacetic acid to form a thioacetate compound of formula (17)

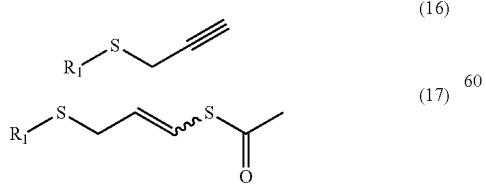

(ii) generating a thiol by treating the compound of formula (17) with a base;

(iii) reacting the thiol with a compound of formula (18), prepared from a tosylate, halide or amide of $R_2$, wherein $R_2$ is as described in claim 1, to produce a compound of formula (19)

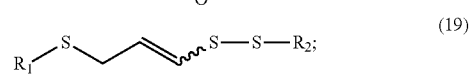

(iv) and oxidizing the compound of formula (19) to produce the compound of formula (2)

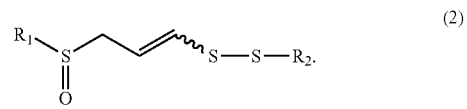

The compound of formula (16) may be acylated with thiolacetic acid via a radical mechanism using a radical initiator, such as azobisisobutyronitrile (AIBN) or a substituted variant thereof, e.g. 1,1'-azobis(cyclohexanecarbonitrile) (ACCN), to initiate the reaction or using palladium (0) coupling of a vinyl halide.

The thiol may be produced by hydrolysis of the compound of formula (17) in an alcoholic solvent using an alkali metal base, such as sodium or potassium hydroxide. The alcoholic solvent may be methanol or ethanol.

The compound of formula (19) may be oxidized by reacting it with an oxidizing agent to produce the compound of formula (2). The oxidizing agent may be m-chloroperoxybenzoic acid (m-CPBA), peroxybenzoic acid or hydrogen peroxide.

The method may further include the step of separating the E- and Z-isomers of the compound of formula (2).

According to a further embodiment of the invention, there is provided the use of a compound of formula (2) in the manufacture of a medicament for the inhibition of the growth of tumour cells and/or for the treatment of cancer.

According to a further embodiment of the invention, there is provided a method of inhibiting the growth of tumour cells and/or treating cancer, the method including the step of administering to a person or animal in need of treatment a pharmaceutically effective amount of a compound of formula (2).

DETAILED DESCRIPTION OF THE INVENTION

A new family of organosulfur compounds of the general formula (2) is described herein,

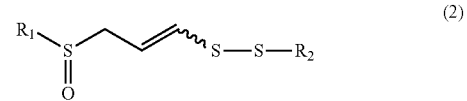

wherein $R_1$ and $R_2$ are
- linear or branched C1-C5 alkyl;
- linear or branched C1-C5 alkenyl, with the proviso that $R_1$ is not prop-1-enyl (allyl);
- substituted linear or branched C1-C5 alkenyl;
- substituted linear or branched C1-C5 alkyl;
- in which the substituents are selected from
  - $OR_3$;
  - $NR_4R_5$;
  - $COOR_6$;
  - $CONR_7R_8$;
  - substituted or unsubstituted aromatic, in particular para-methoxybenzyl or ortho,para-methoxybenzyl;
  - substituted or unsubstituted heteroaromatic,
- in which
  - $R_3$ is selected from H, $COR_9$, para-methoxybenzyl and trialkylsilyl, in
- which $R_9$ is alkyl or substituted alkyl;

$R_4$ and $R_5$ are independently alkyl or $R_4$ and $R_5$ together form a phthalimido group;

$R_6$ is alkyl or substituted alkyl; and $R_7$ and $R_8$ are independently alkyl or substituted alkyl.

More particularly, $R_1$ is not allyl.

Preferred alkyl groups include methyl, ethyl, propyl, butyl, isopropyl and isobutyl. Preferred alkenyl groups include prop-1-enyl (allyl), 1-propenyl, 1-butenyl, 2-butenyl, 3-butenyl and 1-methyl-2-butenyl.

For example, $R_2$ can be prop-1-enyl and $R_1$ can be any one of propyl, 3-hydroxypropyl, 3-phthalimidopropyl, tert-butyl, benzyl, para-methoxybenzyl, 3-(para-methoxybenzyloxy)propyl, 3-(tert-dimethylsilyloxy)propyl; or $R_1$ can be para-methoxybenzyl and $R_2$ can be one of para-methoxybenzyl, benzyl, para-fluorobenzyl; or $R_1$ can be dansyl and $R_2$ can be propyl. More specific examples of compounds of formula (2) are shown in Table 1.

TABLE 1

Examples of compounds of formula (2)

| Compound Number | Substituent at $R_1$ | Substituent at $R_2$ | Compound Name |
|---|---|---|---|
| 3 | propyl | but-3-enyl | (E/Z)-4,5,9-trithiadodeca-1,6-diene-9-oxide |
| 4 | 3-hydroxypropyl | but-3-enyl | (E/Z)-4,8,9-trithiadodeca-6,11-dien-1-ol-4-oxide |
| 5 | 3-phthalimidopropyl | but-3-enyl | (E/Z)-12-phthalimido-4,5,9-trithiadodeca-1,6-diene-9-oxide |
| 6 | tert-butyl | but-3-enyl | (E/Z)-10,10-dimethyl-4,5,9-trithiaundeca-1,6-diene-9-oxide |
| 7 | benzyl | but-3-enyl | (E/Z)-10-phenyl-4,5,9-trithiadeca-1,6-diene-9-oxide |
| 8 | para-methoxybenzyl | but-3-enyl | (E/Z)-10-(p-methoxyphenyl)-4,5,9-trithiadeca-1,6-diene-9-oxide |
| 9 | 3-(para-methoxybenzyloxy)propyl | but-3-enyl | (E/Z)-12-(p-methoxybenzyloxy)-4,5,9-trithiadodeca-1,6-diene-9-oxide |
| 10 | para-methoxybenzyl | para-fluorobenzyl | (E/Z)-1-(p-fluorophenyl)-8-(p-methoxyphenyl)-2,3,7-trithiaocta-4-ene-7-oxide |

TABLE 1-continued

Examples of compounds of formula (2)

| Compound Number | Substituent at $R_1$ | Substituent at $R_2$ | Compound Name |
|---|---|---|---|
| 11 | 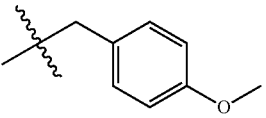 [SMILES: *Cc1ccc(OC)cc1] | 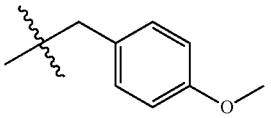 [SMILES: *Cc1ccc(OC)cc1] | (E/Z)-1-(p-methoxyphenyl)-8-(p-methoxyphenyl)-2,3,7-trithiaocta-4-ene-7-oxide |
| 12 | 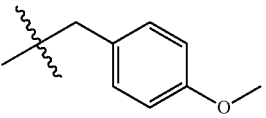 [SMILES: *Cc1ccc(OC)cc1] | 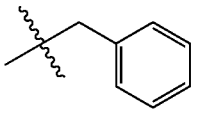 [SMILES: *Cc1ccccc1] | (E/Z)-1-phenyl-8-(p-methoxyphenyl)-2,3,7-trithiaocta-4-ene-7-oxide |
| 13 | 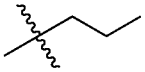 [SMILES: *CCC] | 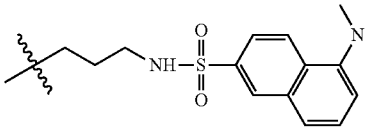 | (E/Z)-1-(dansylamino)-4,5,9-trithiadodeca-6-ene-9-oxide |
| 14 |  | 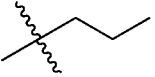 | (E/Z)- 4,5,9-trithiadodeca-6-ene-9-oxide |
| 15 | 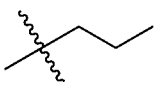 | 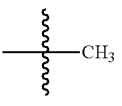 | (E/Z)-2,3,7-trithiadeca-4-ene-7-oxide |

The compounds of the formula (2) can be used for inhibiting the growth of tumour cells. They can therefore be used for treating cancer, such as lung cancer, oesophageal cancer or breast cancer, by administering an effective amount of the compound to a patient in need of treatment. The compound would typically be included in a pharmaceutical composition with a pharmaceutically acceptable carrier. The composition may include a mixture of the E- and Z-isomers of the compound, only the E-isomer or only the Z-isomer.

The compounds can be made by the following method:

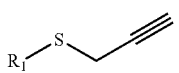
(16)

acylating a compound of formula (16), wherein $R_1$ is as described above, with thiolacetic acid to form a thioacetate compound of formula (17);

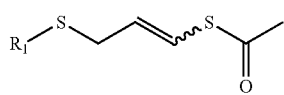
(17)

generating a thiol of (17) by treatment of (17) with a base and then reacting the thiol with a compound of formula (18), prepared from a tosylate, halide or amide of a desired $R_2$-substituent, to produce a compound of formula (19); and

(18)

(19)

oxidizing the compound of formula (19) to produce the compound of formula (2).

The compound of formula (16) can be prepared by reacting a substituted leaving group, such as a substituted halide of formula (25) (where X is a halide), with thiourea to form a corresponding thiourea salt (25a) and, typically in a one-pot reaction, reacting the salt with a base and with a propargyl halide or tosylate to form a compound of formula (26).

$R_1X$ (25)

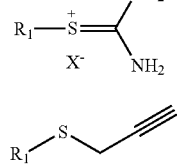
(25a)

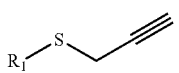
(26)

The substituted halide of formula (25) is generally reacted with the thiourea in an aprotic solvent, such as acetonitrile. The thiouronium salt (25a) is generally hydrolysed in an alcoholic solvent such as methanol or ethanol using an alkali metal base such as sodium or potassium hydroxide. Suitable propargyl halides include propargyl bromide, chloride or iodide.

The compound of formula (16) can be acylated with thiolacetic acid via a radical mechanism using a radical initiator, such as azobisisobutyronitrile (AIBN) or a substituted variant thereof, such as 1,1'-azobis(cyclohexanecarbonitrile) (ACCN), to initiate the reaction or using palladium (0) coupling of a vinyl halide.

The thiol of (17) can be produced by hydrolysis of (17) in an alcoholic solvent, such as methanol or ethanol, using an alkali metal base, such as sodium or potassium hydroxide. The compound of formula (19) can be oxidized by reaction with an oxidizing agent, such as m-chloroperoxybenzoic acid (m-CPBA), peroxybenzoic acid or hydrogen peroxide, to produce the compound of formula (2).

The E- and Z-isomers may, in certain cases, be in the form of an inseparable mixture and, in other cases, in the form of a separable mixture. In the cases where the isomers are in the form of a separable mixture, they may be separated. Suitable separation methods include silica gel column chromatography; preparative TLC and high performance liquid chromatography (HPLC).

Example

The invention will now be described in more detail by way of the following non-limiting example.

The preparation of (E/Z)-4,5,9-trithiadodeca-1,6-diene-9-oxide (3) is described below. It will, however, be apparent to a person skilled in the art that other compounds of formula (2) can readily be made using the same method.

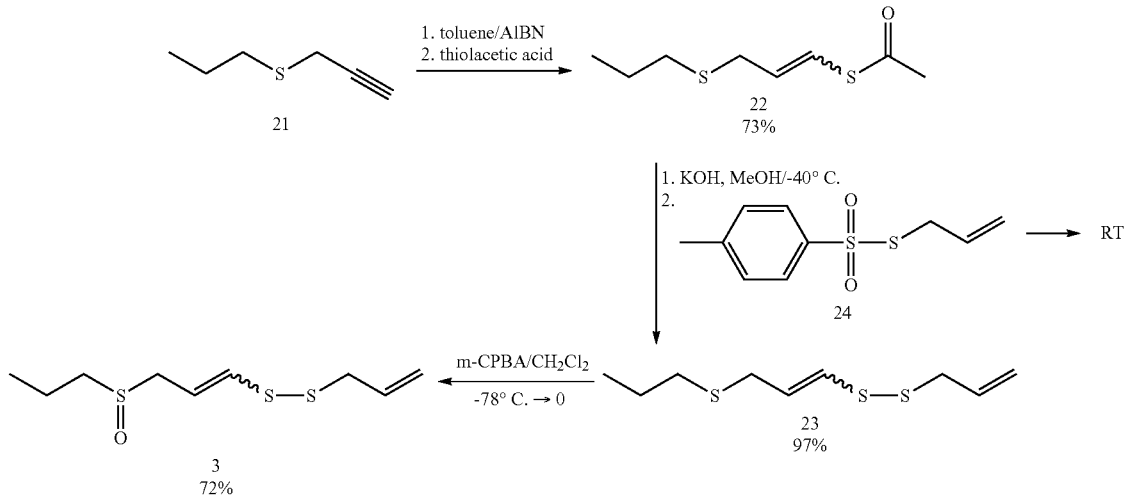

Scheme 1: Synthetic route to synthesize analogue (3)

A mixture of the E- and Z-isomers of the compound of formula (2) can be produced by this method. The E- and Z-isomers of the compound of formula (2), in which $R_2$ is allyl, are represented by formula (20.1) and formula (20.2), respectively. The applicant has found that the formation of the Z-isomer is generally favoured over the E-isomer in a 2:1 ratio.

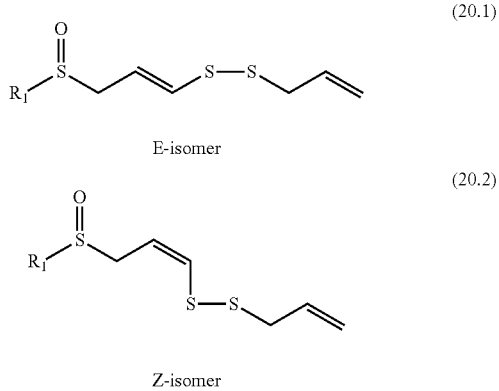

In the above synthesis, 4-thia-1-heptyne (21) is converted to the thioester (E,Z)—S-1-(4-hiahept-1-enyl)ethanethioate (22) with thiolacetic acid via radical addition using 1,1'-azobis(cyclohexanecarbonitrile) (ACCN) in toluene and as a 2:1 E:Z mixture of the thioester products (22). The thiol anion of (22) is then formed in KOH/methanol at −40° C. (low temperature bath with acetonitrile/$N_2$) and then alkylated using the allylated thiotosylate (24) to produce the disulfide 4,5,9-trithiadodeca-1,6-diene (23) in high yield. The sulfide is than oxidized up to the sulfoxide at low temperature with m-chloroperbenzoic acid in dichloromethane to give analogue (3) in 51% overall yield for 3 steps. The E- and Z-isomers were separated using silica gel column chromatography.

The detailed stepwise reaction sequence to produce compound (3) is shown below. All other analogues are synthesized according to the same procedure.

S-1-(4-Thiahept-1-enyl)ethanethioate (22)

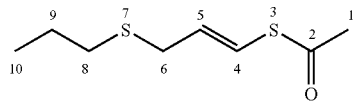

Thiolacetic acid (T35 g, 96.6 mmol), alkyne 21 (10.0 g, 87.6 mmol) and 1,1'-azobis(cyclohexanecarbonitrile) (ACCN) (2.14 g, 8.76 mmol) were refluxed in toluene at 80° C. under $N_2$ for 2 h. Toluene was then removed under vacuum and the residue dried on a pump to give an orange oil, which was purified directly on a silica-gel column using neat petroleum ether as eluent to give compound 22 (9.80 g, 80% based on recovery of 2.64 g of alkyne 21 and as a 3:2 mixture of Z/E stereoisomers: $v_{max}/cm^{-1}$ 2957 (C—H), 1698 (C=O), 634 (C—S):

Z-22 $\delta_H$ (400 MHz, $CDCl_3$) 0.95 (3H, t, J 7.4 Hz, H-10), 1.60 (2H, m, H-9), 2.37 (3H, s, H-1), 2.41 (2H, t, J 7.3 Hz, H-8), 3.16 (2H, dd, J 1.3, 7.8 Hz, H-6), 5.85 (1H, dt, J 7.8, 10.4 Hz, H-5), 6.65 (1H, dd, J 1.3, 10.4 Hz, H-4); $\delta_C$ (100 MHz, $CDCl_3$), 13.4 (C-10), 22.8 (C-9), 30.8 (C-1), 31.0 (C-6), 33.2 (C-8), 119.1 (C-4), 130.5 (C-5), 191.2 (C-9).

E-22 $\delta_H$ (400 MHz, $CDCl_3$), 0.96 (3H, t, J 7.4 Hz, H-10), 1.60 (2H, m, H-9), 2.32 (3H, s, H-1), 2.41 (2H, t, J 7.3 Hz, H-8), 3.21 (2H, dd, J 1.3, 7.8 Hz, H-6), 5.80 (1H, dt, J 7.8 15.7 Hz, H-5), 6.52 (1H, dt, J 1.3, 15.7 Hz, H-4); $\delta_C$ (100 MHz, $CDCl_3$), 13.4 (C-10), 22.6 (C-9), 30.5 (C-1), 33.0 (C-8), 34.0 (C-6), 118.8 (C-4), 130.5 (C-5), 192.8 (C-9).

(E,Z)-4,5,9-trithiadodeca-1,6-diene (23)

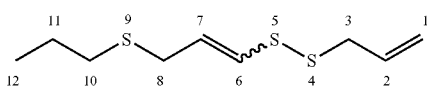

KOH (1.44 g, 25.2 mmol) was dissolved in methanol (20 ml) at 0° C. and added dropwise to thioate ester 22 (2.40 g, 12.6 mmol) in methanol (10 ml) at −30° C. under $N_2$. The reaction was left stirring for 20 min before cooling to −78° C., whereupon S-prop-2-enyl 4-methylbenzenesulfonothioate (2.94 g, 12.9 mmol in methanol (5.0 ml) was added dropwise. The reaction was allowed to warm to 0° C. and left stirring for 2 h before quenching with aqueous ammonium chloride (20 ml). Water (40 ml) was added and the product was then extracted with $CH_2Cl_2$ (3×50 ml). The $CH_2Cl_2$ extracts were washed with saturated brine solution (2×20 ml), dried and reduced under vacuum. The resultant orange liquid was purified on a silica-gel column using petroleum ether as eluent to give compound 23 as a 3:2 mixture of Z:E geometrical stereoisomers (2.46 g, 89% yield):

Z-23 $\delta_H$ (400 MHz, $CDCl_3$) 0.99 (3H, t, J 7.3 Hz, H-12), 1.63 (2H, m, H-11), 2.48 (2H, t, J 7.3 Hz, H-10), 3.27 (2H, dd, J 1.1, 7.4 Hz, H-8), 3.37 (2H, m, H-3), 5.18 (2H, m, H-1), 5.69 (1H, dt, J 7.4, 9.7 Hz, H-7), 5.87 (1H, m, H-2), 6.23 (1H, dt, J 1.1, 9.7 Hz, H-6); $\delta_C$ (100 MHz, $CDCl_3$), 13.5 (C-12), 23.0 (C-11), 29.5 (C-8), 33.4 (C-10), 42.1 (C-3), 118.9 (C-1), 128.7 (C-7), 131.7 (C-6), 132.9 (C-2).

E-23 $\delta_H$ (400 MHz, $CDCl_3$) 0.99 (3H, t, J 7.3 Hz, H-12), 1.60 (2H, m, H-11), 2.45 (2H, t, J 7.3 Hz, H-10), 3.19 (2H, dd, J 1.2, 7.7 Hz, H-8), 3.35 (2H, m, H-3), 5.17 (1H, d, J 8.9 Hz, H-1 trans), 5.29 (1H, d, J 16.8 Hz, H-1 cis), 5.86 (2H, m, H-2, H-7), 6.11 (1H, dt, J 1.2, 14.6 Hz, H-6); $\delta_C$ (100 MHz, $CDCl_3$), 13.5 (C-12), 22.7 (C-11), 33.1 (C-10), 33.5 (C-8), 41.3 (C-3), 118.9 (C-1), 127.5 (C-7), 128.6 (C-6), 132.8 (C-2).

(E,Z)-4,5,9-Trithiadodeca-1,6-diene 9-oxide (3)

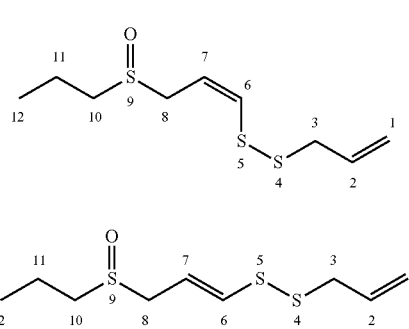

m-Cpba (396 mg, 2.30 mmol) was dissolved in $CH_2Cl_2$ (5 ml) and added dropwise to compound 23 (460 mg, 2.09 mmol) in $CH_2Cl_2$ (5 ml) at −78° C. under $N_2$. The reaction was allowed to warm to room temperature and left stirring for 3 h, before quenching with saturated aq. sodium bicarbonate (15 ml) and extracting with ethyl acetate (3×30 ml). The organic extracts were dried with $MgSO_4$, and the solvent removed under vacuum. The resultant residue was then purified on a silica-gel column using 40% ethyl acetate in petroleum ether as eluent to give compound 3 (400 mg, 82%) as a separable 3:2 mixture of ZE geometrical stereoisomers.

Z-3a IR $v_{max}$ (neat)/$cm^{-1}$ 2976 (HC=C), 2246 (HC—C aliphatic), 1368 (C=C), 1302 (S=O), 651 (C—S), 450 (S—S); $\delta_H$ (400 MHz, $CDCl_3$) 1.08 (3H, t, J 7.3 Hz, H-12), 1.81 (2H, m, H-11), 2.61 (1H, dt, J 8.2, 13.7 Hz, H-10a), 2.71 (1H, dt, J 8.2, 13.7 Hz, H-10b), 3.37 (2H, m, H-3), 3.56 (1H, dd, J 8.1, 13.2, Hz, H-8a), 3.63 (1H, dd, J 8.1, 13.2, Hz, H-8b), 5.16 (2H, m, H-1), 5.76 (1H, dt, J 8.1, 9.2, Hz, H-7), 5.84 (1H, m, H-2), 6.54 (1H, d, J 9.2 Hz, H-6); $\delta_C$ (100 MHz, $CDCl_3$), 13.4 (C-12), 16.2 (C-11), 42.1 (C-3), 50.9 (C-8), 53.5 (C-10), 118.5 (C-7), 119.2 (C-1), 132.8 (C-2), 138.2 (C-6).

E-3b IR $v_{max}$ (neat)/$cm^{-1}$ 2970(HC=C), 2232 (HC—C aliphatic), 1400 (C=C), 1018 (S=O), 644 (C—S), (S—S). $\delta_H$ (400 MHz, $CDCl_3$), 1.06 (3H, t, J 7.3 Hz, H-12), 1.80 (2H, m, H-11), 2.61 (2H, m, H-10), 3.33 (2H, m, H-3), 3.43 (1H, dd, J 7.9, 13.2 Hz, H-8a), 3.51 (1H, dd, J 7.9, 13.2 Hz, H-8b), 5.15 (2H, m, H-1), 5.82 (1H, m, H-2), 5.91 (1H, dt, J 7.9, 14.6 Hz, H-7), 6.34 (1H, d, J 14.6, H-6); $\delta_C$ (100 MHz, $CDCl_3$), 13.3 (C-12), 16.1 (C-11), 41.2 (C-3), 53.0 (C-10), 54.5 (C-8), 117.1 (C-7), 119.1 (C-1), 132.4 (C-2), 134.2 (C-6).

Other compounds synthesized by this synthetic route include:

(E/Z)-4,5,9-trithiadodeca-1,6-diene-9-oxide (3), or (E/Z)-4,8,9-trithiadodeca-6,11-diene-1-ol-4-oxide (4), (E/Z)-12-phthalimido-4,5,9-trithiadodeca-1,6-diene-9-oxide (5), (E/Z)-10,10-dimethyl-4,5,9-trithiaundeca-1,6-diene-9-oxide (6), E/Z)-10-phenyl-4,5,9-trithiadeca-1,6-diene-9-oxide (7), (EJZ)-10-(p-methoxyphenyl)-4,5,9-trithiadeca-1,6-diene-9-oxide (8), (E/Z)-12-(p-methoxybenzyloxy)-4,5,9-trithiadodeca-1,6-diene-9-oxide (9), (E/Z)-1-(p-fluorophenyl)-8-(p-methoxyphenyl)-2,3,7-trithiaocta-4-ene-7-oxide (10), (E/Z)-1-(p-methoxyphenyl)-8-(p-methoxyphenyl)-2,3,7- trithiaocta-4-ene-7-oxide (11), (E/Z)-1-phenyl-8-(p-methoxyphenyl)-2,3,7-trithiaocta-4-ene-7-oxide (12), (E/Z)-1-(dansylamino)-4,5,9-trithiadodeca-6-ene-9-oxide (13), (E/Z)-4,5,9-trithiadodeca-6-ene-9-oxide (14) and (E/Z)-2,3,7-trithiadeca-4-ene-7-oxide (15).

In Vitro Anti-Cancer Activity

The compounds were evaluated for their in vitro ability to inhibit cell growth of cultured tumour cells using the 3-(4,5-dimethylthiazol-2-yl)-2,5-diphenyltetrazolium bromide (MTT) assay. These cell types include:

1. WI38 cells which are normal embryonic lung fibroblasts;
2. CT-1 cells which are transformed WI38 fibroblasts;
3. WHCO1 cells which are oesophageal epithelial cancer cells; and
4. EPC2 cells which are normal oesophageal epithelial cells; and
5. MDA-MB-231 cells which are human breast epithelial cancer cells; and
6. MCF12a cells which are normal human breast epithelial cells.

One oesophageal squamous cell carcinoma cell line WHCO1 originally established from surgical biopsies of primary oesophageal squamous cell carcinomas, a transformed fibroblast cell line CT-1 or human breast epithelial cells MDA-MB-231 were cultured in DMEM containing 10% foetal calf serum and 1% penicillin and streptomycin at 37° C. in a humidified atmosphere of 5% $CO_2$. For the MTT assay, $3\times10^3$ cells were plated in 96-well plates in 90 μL DMEM per well. Compounds solubilized in DMEM+1% DMSO (10 μl) were added to cells and DMEM+1% DMSO, (10 μl) alone was added to the control to give a final concentration of 0-200 μM compound and 0.1% DMSO. After 48 hours incubation period, 10 μL of the MTT labelling reagent (final concentration 0.45 mg/ml) was added to each well and incubated for 4 hours in a humidified atmosphere at 37° C. One hundred micro litres of the solubilization solution was added to each well and the plates were incubated overnight at 37° C. The spectrophotometric absorbance of the wells was measured at 595 nm using a microtiter plate reader.

The results are displayed as in vitro $IC_{50}$'s in Table 2, defined as the concentration of drug required to inhibit cell growth of half of the cell population.

TABLE 2

In vitro $IC_{50}$ Values Obtained for Ajoene-Analogues on CT-1, WHCO1 and MDA cell lines

| | CT1 | | | WHCO1 | | | MDA | | |
|---|---|---|---|---|---|---|---|---|---|
| Compound number | n | $IC_{50}$/ μM | 95% CI | n | $IC_{50}$/ μM | 95% CI | n | $IC_{50}$/ μM | 95% CI |
| E-ajoene | 6 | 17.6 | 17.4-17.8 | 6 | 20.9 | 20.7-21.1 | | ND | |
| Z-ajoene | 6 | 15.5 | 15.3-15.6 | 6 | 20.5 | 20.2-20.8 | | ND | |
| E-3 | 5 | 26.7 | 26.5-26.9 | 10 | 35.8 | 35.5-36.0 | 2 | 25.9 | 25.5-26.2 |
| Z-3 | 5 | 17.0 | 16.8-17.2 | 12 | 21.6 | 21.5-21.7 | 5 | 19.2 | 19.0-19.3 |
| E-4 | 5 | 23.1 | 23.0-23.3 | 6 | 26.8 | 24.7-29.2 | | ND | |
| Z-4 | 6 | 22.8 | 22.5-23.1 | 6 | 37.9 | 34.5-41.6 | | ND | |
| E-5 | 4 | 95.9 | 95.0-96.8 | 5 | 68.9 | 61.2-77.6 | | ND | |
| Z-5 | 4 | 34.6 | 34.3-34.9 | 6 | 36.0 | 32.9-39.5 | | ND | |
| EZ-6 | 5 | 33.1 | 32.5-33.6 | 6 | 25.4 | 23.4-27.6 | | ND | |
| EZ-7 | 5 | 16.6 | 16.5-16.7 | 6 | 8.8 | 8.7-8.8 | | ND | |
| EZ-8 | 12 | 11.2 | 11.1-11.3 | 6 | 7.12 | 7.07-7.17 | 3 | 6.60 | 5.85-7.35 |
| E-9 | 5 | 23.5 | 23.2-23.8 | 8 | 19.1 | 18.9-19.3 | | ND | |
| Z-9 | 6 | 21.7 | 21.6-21.9 | 6 | 16.9 | 16.7-17.0 | | ND | |
| EZ-10 | | ND | | 3 | 13.6 | 13.5-13.7 | | ND | |
| EZ-11 | | ND | | 2 | 1.34 | 1.33-1.36 | 4 | 0.82 | 0.82-0.83 |
| EZ-12 | | ND | | 2 | 3.05 | 3.01-3.10 | 1 | 1.19 | |
| EZ-13 | 5 | 17.7 | 17.5-17.9 | 3 | 14.2 | 14.1-14.3 | | 42.6 | |
| E-14 | 4 | 9.32 | 9.11-9.36 | 4 | 33.8 | 34.2-33.4 | | ND | |
| Z-14 | | ND | | | ND | | | ND | |
| E-15 | 6 | 10.3 | 10.2-10.4 | 5 | 47.4 | 47.1-47.7 | | ND | |
| Z-15 | | ND | | | ND | | | ND | |

ND = not determined
n = number on independent experimental determinations
$IC_{50}$ = Inhibitory concentration of drug used to cause 50% inhibition of cell growth
95% CI = 95% confidence interval From the in vitro data, it was found that both the Z- and E-isomers of ajoene have equivalent activity at inhibiting cell growth of CT-1 and WHCO1 cancer cells. For the synthesized ajoene analogues, with the exception of analogue 4 on WHCO1 cells, the Z-isomers are all more active at inhibiting cancer cell growth than their corresponding E-isomers.

Some of the analogues synthesized display superior activity to ajoene. In particular, the most active analogue EZ-11, is fifteen times more active than ajoene at inhibiting growth of WHCO1 oesophageal cancer cells in vitro. The four most active drug candidates that display $IC_{50}$ activities under 10 μM are shown below.

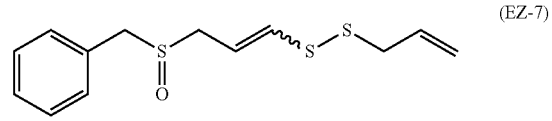

IC50 (WHCO1) = 8.8 uM

-continued

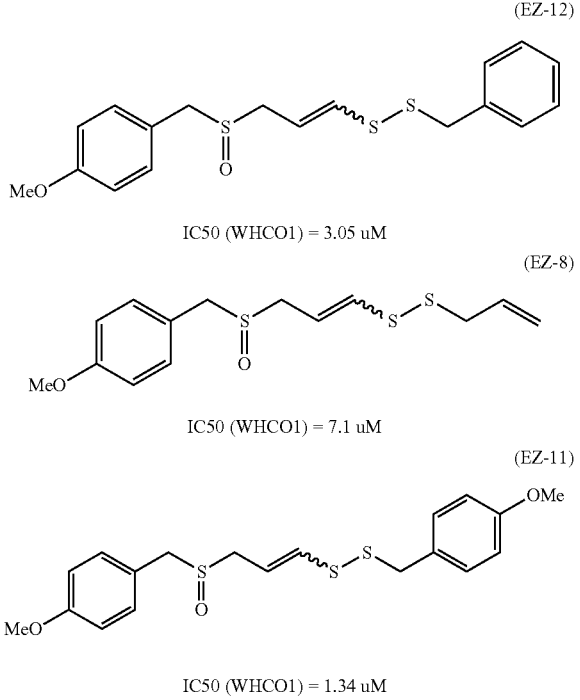

(EZ-12)
IC50 (WHCO1) = 3.05 uM (EZ-8)
IC50 (WHCO1) = 7.1 uM (EZ-11)
IC50 (WHCO1) = 1.34 uM

It appears that strongly electron donating groups and/or lipophilic groups at $R_{10}$, $R_{11}$, $R_{12}$ and $R_{13}$ positions in the compound of formula (27) are important for strong in vitro activity. It also appears that lipophilic substituents at $R_1$ and $R_2$ in formula (2) are also important for good in vitro anti-cancer activity.

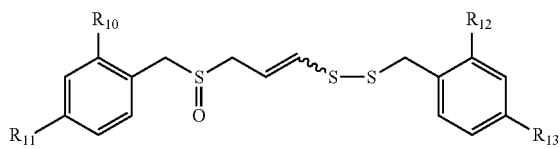

Formula (27): General structure of the active-class of compounds with $R_{10}$-$R_{13}$ being electron donating/lipophilic groups.

In summary, the applicant has developed a synthetic route to access compounds of formula (2), being analogues of ajoene, with varying substituents at the $R_1$ and $R_2$ positions. The strongest drug candidates synthesized to date are those compounds with either benzyl or para-methoxybenzyl groups at positions $R_1$ and/or $R_2$ of formula (2). These compounds display in vitro $IC_{50}$ killing activities on WHCO1 and MDA cancer cells at drug concentrations under 10 μM.

The invention claimed is:
1. A compound of formula (2)

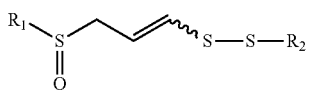

(2)

wherein:
$R_1$ is propyl, butyl, isopropyl, or isobutyl; dansyl;
  substituted linear or branched C1-C5 alkenyl; or
  substituted linear or branched C1-C5 alkyl;
    in which the substituents are selected from
      $OR_3$;
      $NR_4R_5$; and
      $CONR_7R_8$;
    substituted or unsubstituted aromatic;
    substituted or unsubstituted heteroaromatic,
    in which
      $R_3$ is selected from H, $COR_9$, para-methoxybenzyl, and trialkylsilyl, in which $R_9$ is alkyl or substituted alkyl;
      $R_4$ and $R_5$ are independently alkyl or $R_4$ and $R_5$ together form a phthalimido group;
      $R_7$ and $R_8$ are independently alkyl or substituted alkyl;
and $R_2$ is
  linear or branched C1-C5 alkyl;
  linear or branched C1-C5 alkenyl;
  substituted linear or branched C1-C5 alkenyl; or
  substituted linear or branched C1-C5 alkyl;
  in which the substituents are selected from
    $OR_3$;
    $NR_4R_5$; and
    $CONR_7R_8$;
  substituted or unsubstituted aromatic;
  substituted or unsubstituted heteroaromatic;
  in which
    $R_3$ is selected from H, $COR_9$, para-methoxybenzyl, and trialkylsilyl, in which $R_9$ is alkyl or substituted alkyl;
    $R_4$ and $R_5$ are independently alkyl or $R_4$ and $R_5$ together form a phthalimido group;
    $R_7$ and $R_8$ are independently alkyl or substituted alkyl,
wherein the compound of formula (2) excludes (E/Z)-4,5,9-trithiadodeca-1,6-diene-9-oxide.

2. A compound according to claim 1, wherein the alkyl groups for $R_2$, $R_4$, $R_5$, $R_7$, $R_9$, and $R_9$ are independently selected from the group consisting of methyl, ethyl, propyl, butyl, isopropyl and isobutyl.

3. A compound according to claim 1, wherein the alkenyl groups for $R_2$ or the substituted linear or branched C1-C5 alkenyl are independently selected from the group consisting of prop-1-enyl (allyl), 1-propenyl, 1-butenyl, 2-butenyl, 3-butenyl and 1-methyl-2-butenyl.

4. A compound according to claim 1, wherein $R_1$ is selected from the group consisting of propyl, 3-hydroxypropyl, 3-phthalimidopropyl, tert-butyl, benzyl, para-methoxybenzyl, ortho,para-methoxybenzyl, 3-(para-methoxybenzyloxy)propyl, dansyl and 3-(tert-dimethylsilyloxy)propyl.

5. A compound according to claim 1, wherein $R_2$ is selected from the group consisting of propyl, prop-1-enyl, para-methoxybenzyl, ortho,para-methoxybenzyl, benzyl, para-fluorobenzyl, and (dansylamino)-propyl.

6. A compound according to claim 1, wherein $R_1$ is selected from the group consisting of propyl, 3-hydroxypropyl, 3-phthalimidopropyl, tert-butyl, benzyl, para-methoxybenzyl, ortho,para-methoxybenzyl, 3-(para-methoxybenzyloxy)propyl and 3-(tert-dimethylsilyloxy)propyl and $R_2$ is prop-1-enyl.

7. A compound according to claim 1, wherein $R_1$ is para-methoxybenzyl or ortho,para-methoxybenzyl and $R_2$ is selected from the group consisting of para-methoxybenzyl, ortho,para-methoxybenzyl, benzyl and para-fluorobenzyl.

8. A compound according to claim 1, wherein
$R_1$ is dansyl and $R_2$ is propyl; or
$R_1$ is propyl and $R_2$ is (dansylamino)-propyl.

9. A compound according to claim 1, which is:
(E/Z)-4,8,9-trithiadodeca-6,11-diene-1-ol-4-oxide,
(E/Z)-12-phthalimido-4,5,9-trithiadodeca-1,6-diene-9-oxide,
(E/Z)-10,10-dimethyl-4,5,9-trithiaundeca-1,6-diene-9-oxide,
(E/Z)-10-phenyl-4,5,9-trithiadeca-1,6-diene-9-oxide,
(E/Z)-10-(p-methoxyphenyl)-4,5,9-trithiadeca-1,6-diene-9-oxide,
(E/Z)-12-(p-methoxybenzyloxy)-4,5,9-trithiadodeca-1,6-diene-9-oxide,
(E/Z)-1-(p-fluorophenyl)-8-(p-methoxyphenyl)-2,3,7-trithiaocta-4-ene-7-oxide,
(E/Z)-1-(p-methoxyphenyl)-8-(p-methoxyphenyl)-2,3,7-trithiaocta-4-ene-7-oxide,
(E/Z)-1-phenyl-8-(p-methoxyphenyl)-2,3,7-trithiaocta-4-ene-7-oxide,
(E/Z)-1-(dansylamino)-propyl-4,5,9-trithiadodeca-6-ene-9-oxide,
(E/Z)-4,5,9-trithiadodeca-6-ene-9-oxide, or
(E/Z)-2,3,7-trithiadeca-4-ene-7-oxide.

10. A pharmaceutical composition comprising a compound of claim 1 and a pharmaceutically acceptable carrier.

11. A method of making a compound of formula (2) according to claim 1, the method including the steps of:
(i) acylating a compound of formula (16), wherein $R_1$ is as described in claim 1, with thioacetic acid to form a thioacetate compound of formula (17);

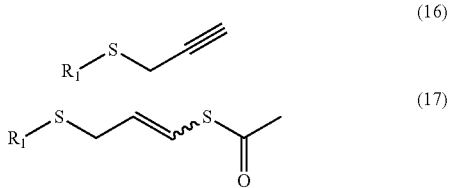

(ii) generating a thiol by treating the compound of formula (17) with a base;
(iii) reacting the thiol with a compound of formula (18), prepared from a tosylate, halide or amide of $R_2$, wherein $R_2$ is as described in claim 1, to produce a compound of formula (19)

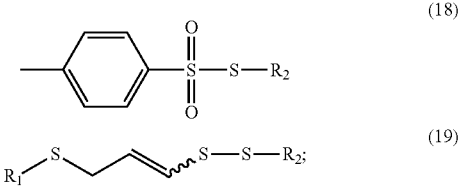

(iv) and oxidizing the compound of formula (19) to produce the compound of formula (2)

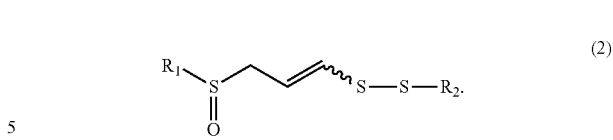

12. A method according to claim 11, wherein the compound of formula (16) is acylated with thiolacetic acid via a radical mechanism using a radical initiator to initiate the reaction.

13. A method according to claim 12, wherein the radical initiator is azobisisobutyronitrile (AIBN) or a substituted variant thereof.

14. A method according to claim 13, wherein the substituted variant is 1,1'-azobis(cyclohexanecarbonitrile) (ACCN).

15. A method according to claim 11, wherein the compound of formula (16) is acylated with thiolacetic acid using palladium (0) coupling of a vinyl halide.

16. A method according to claim 11, wherein the thiol is produced by hydrolysis of the compound of formula (17) in an alcoholic solvent using an alkali metal base.

17. A method according to claim 16, wherein the alkali metal base is sodium or potassium hydroxide.

18. A method according to claim 16, wherein the alcoholic solvent is methanol or ethanol.

19. A method according to claim 11, wherein the compound of formula (19) is oxidized by reacting it with an oxidizing agent to produce the compound of formula (2).

20. A method according to claim 19, wherein the oxidizing agent is selected from the group consisting of m-chloroperoxybenzoic acid (m-CPBA), peroxybenzoic acid and hydrogen peroxide.

21. A method according to claim 11, which further includes the step of:
(v) separating the E- and Z-isomers of the compound of formula (2).

22. A method of inhibiting the growth of lung tumour cells, oesophageal tumour cells, breast tumour cells, bladder colorectal, hepatic, nasopharyngeal, gastric, prostate, pancreatic, lymphoma, leukemia, hepatocarcinoma, and skin tumour cells and/or treating lung cancer, oesophageal cancer, breast cancer, bladder colorectal, hepatic, nasopharyngeal, gastric, prostate, pancreatic, lymphoma, leukemia, hepatocarcinoma, and skin cancer, the method including the step of administering to a person or animal in need of treatment a pharmaceutically effective amount of a compound of claim 1.

23. A method according to claim 22, wherein the cancer is selected from the group consisting of lung cancer, oesophageal cancer, cervical cancer and breast cancer.

24. A method of inhibiting the growth of lung tumour cells, oesophageal tumour cells, breast tumour cells, bladder colorectal, hepatic, nasopharyngeal, gastric, prostate, pancreatic, lymphoma, leukemia, hepatocarcinoma, and skin tumour cells and/or treating lung cancer, oesophageal cancer, breast cancer, bladder colorectal, hepatic, nasopharyngeal, gastric, prostate, pancreatic, lymphoma, leukemia, hepatocarcinoma, and skin cancer, the method including the step of administering to a person or animal in need of treatment a pharmaceutically effective amount of a pharmaceutical composition according to claim 10.

* * * * *